United States Patent [19]

LeVeen

[11] Patent Number: 4,491,136
[45] Date of Patent: Jan. 1, 1985

[54] DISPOSABLE CIRCUMCISION DEVICE

[76] Inventor: Harry H. LeVeen, 800 Poly Pl., Brooklyn, N.Y.

[21] Appl. No.: 218,548

[22] Filed: Dec. 22, 1980

Related U.S. Application Data

[63] Continuation of Ser. No. 911,235, May 31, 1978, abandoned, which is a continuation of Ser. No. 368,369, Jun. 8, 1973, abandoned, which is a continuation-in-part of Ser. No. 338,392, Mar. 5, 1973, abandoned.

[51] Int. Cl.³ .............................................. A61B 17/00
[52] U.S. Cl. .................................... 128/346; 128/305
[58] Field of Search ................................ 128/305, 346

[56] References Cited

U.S. PATENT DOCUMENTS

| | | | |
|---|---|---|---|
| 2,076,468 | 4/1937 | Breck | 128/305 |
| 2,272,072 | 2/1942 | Ross | 128/346 |
| 2,544,037 | 3/1951 | Moseley | 128/346 |
| 2,561,176 | 7/1951 | Buckingham | 128/346 |
| 3,111,124 | 11/1963 | Rodbard | 128/346 |
| 3,625,218 | 12/1971 | Valinoti | 128/303.14 |
| 3,802,439 | 4/1974 | Baumgarten | 128/346 |

*Primary Examiner*—Michael H. Thaler
*Attorney, Agent, or Firm*—Brooks, Haidt, Haffner & Delahunty

[57] ABSTRACT

A unique circumcision device is disclosed which facilitates cutting of the foreskin of the penis and promotes complete healing of the incision without recourse to sutures and can be performed by one person without assistance.

The device in its preferred form compresses in combination a male member which covers the head of the penis and has frictionally attached at one end a ring having an annular groove therein, a female member which fits over the shaft of the penis which compresses a plastic ring having a flexible wall such that its inside diameter can be increased or diminished in response to external compressive force exerted therein or removed therefrom.

The male member is inserted and fits under the foreskin and the female member over the foreskin so that the plastic ring of the female member can be moved up to a positon in register which superimposes it over the ring on the male member underneath the foreskin with the foreskin caught in between the two. An external compression member initially surrounds the plastic flexible ring of the female member and after the inner and outer rings are in register the compression member is removed from the female ring member causing the plastic outer ring of the female member to shrink in diameter and compress the tissue of the foreskin against the shaft of the penis while the excess foreskin is surgically excised.

4 Claims, 10 Drawing Figures

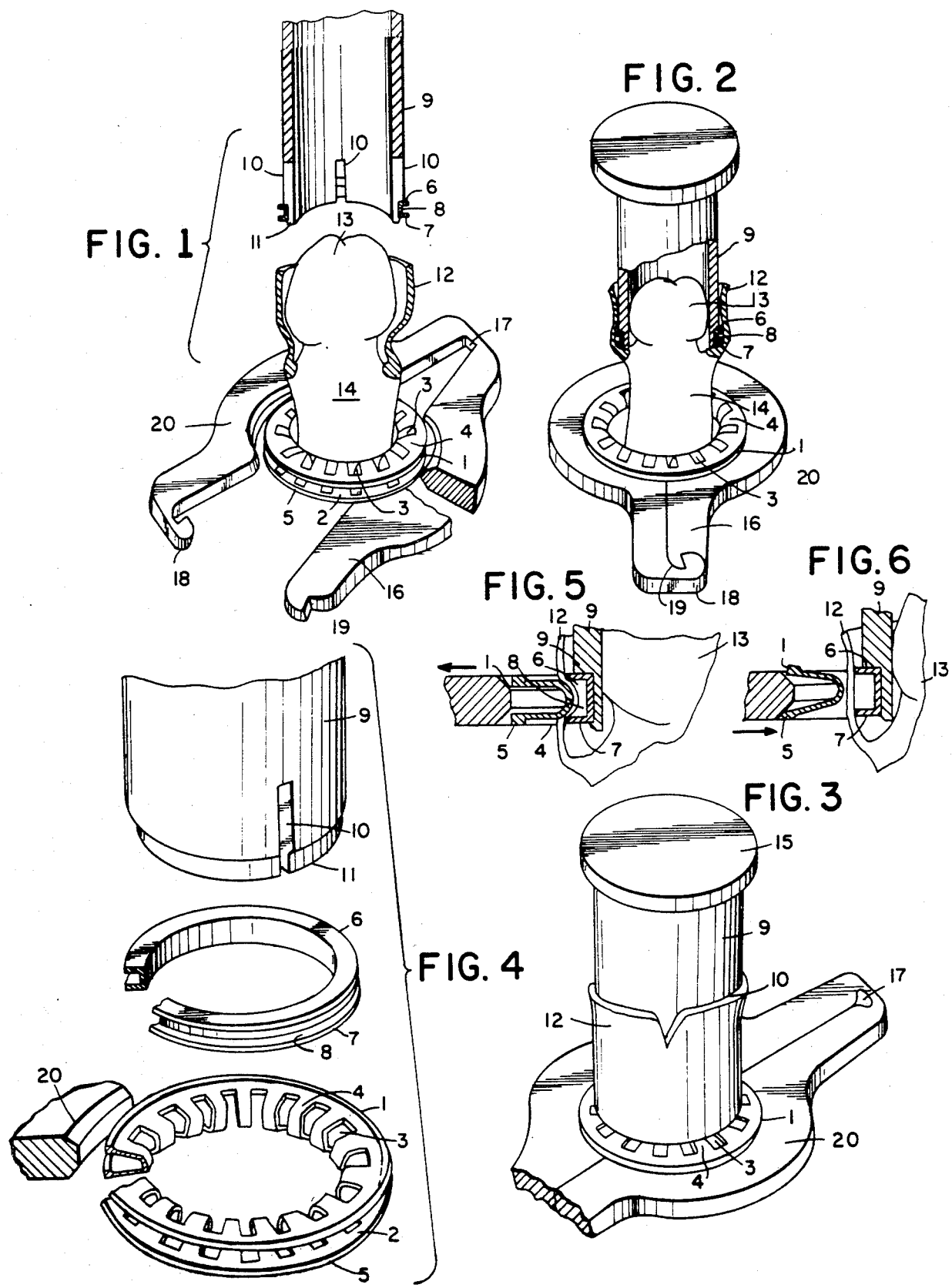

DISPOSABLE CIRCUMCISION DEVICE

RELATED APPLICATIONS

This application is a continuation of application Ser. No. 911,235 filed on May 31, 1978, now abandoned, as a continuaion of application Ser. No. 368,369, filed on June 8, 1973, now abandoned, which was in turn a continuation-in-part of application Ser. No. 338,392, filed March 5, 1973, now abandoned.

BACKGROUND OF THE INVENTION

For many years the art of circumcision has been practiced for both health and religious reasons but until recently the means by which the operation was practiced was not scientifically and painlessly developed. Fairly recently, however, there has appeared on the market a rather simple device which involves the tying of a cord or string about the penis at an approximate point between the selected cutting line where the foreskin is removed and the main shaft of the penis. Since this is generally done in the hospital on newborn babies the wound is tied off and bleeding is halted to a degree which in large measure depends on the accuracy of the tie of the cord. This of course requires two nurses or a nurse and a doctor and is only as accurate as the security of the tie made. One person must use both hands to tie the cord about the penis while the other holds the child still or restrains his movement.

It has been found that failure to circumcise infants can lead to various problems in later life such as prostate gland problems in the male and where the male is married it has even been claimed that uterine cancer in his wife is related to an unclean foreskin which has not been removed by circumcision. However, when the foreskin is removed in other than newborn infants additional problems arise with respect to the healing of the excised tissue. A present means to prevent this bleeding and promote proper joinder of the tissue is to suture the same, but in this area of the body this is obviously a very sore and delicate technique.

In view of this present set of circumstances therefore it would be of great value to the medical profession to have available a simple device for use in circumcisions which would promote the healing of the cut end of the foreskin and forestall bleeding therefrom without need to resort to suturing of the tissue. Thus the primary objective of the present invention is to provide just such a device and to teach a method for doing circumcisions which involves its use.

BRIEF DESCRIPTION OF THE SEVERAL FIGURES OF THE DRAWING

The invention will be described by reference to the several FIGS. 1-10 of the drawing.

FIG. 1 shows a perspective view of the female member of the device as it is first positioned about the penis with the compression clamp 16 open and unlatched.

FIG. 2 shows a perspective view of the clamp 16 in the closed position and the support tube 9 pushed underneath the foreskin 12.

FIG. 3 is another perspective view of the male tube 2 and the female member fingers 4 in register with the inner ring (6,7,8) interposed beneath the skin.

FIG. 4 is an exploded view of the arrangement described in FIG. 3 showing the tube, the inner ring and the outer ring.

FIGS. 5 and 6 are enlarged, fragmentary cross-sectional views of the tube, inner ring and outer ring.

Figure 7:
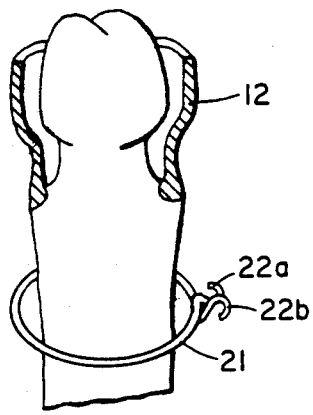

FIG. 7 is a perspective view of an alternate embodiment wherein the compression, i.e., fingers 4 and spaces 3 are replaced by a clamp 21 to contact and surround the outside of the foreskin.

Figure 8:
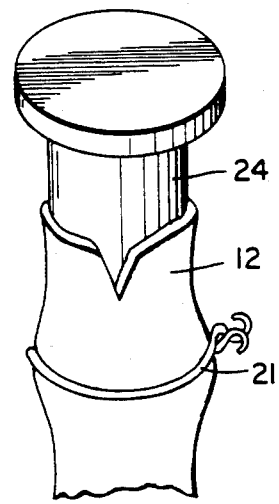

FIG. 8 is a perspective view of clamp 21 in register with inner tube 24.

Figure 9:
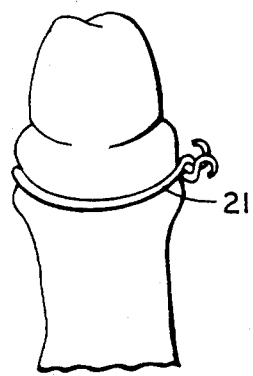

FIG. 9 is a perspective view of the foreskin removed and clamped.

Figure 10:
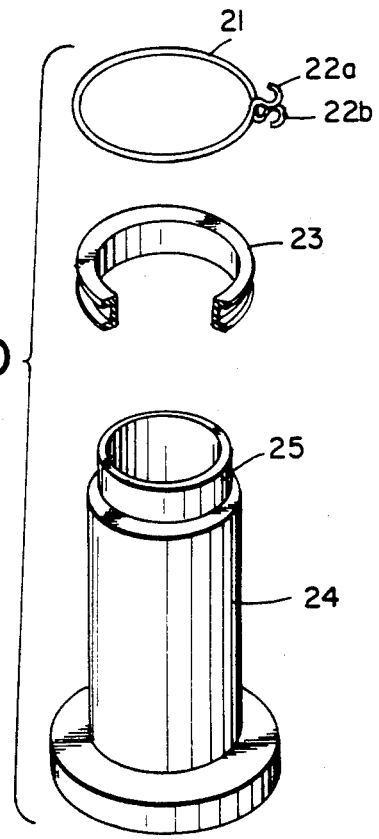

FIG. 10 is an exploded view of the several elements of the latter embodiment of the invention.

BRIEF DESCRIPTION OF THE INVENTION

Accordingly a circumcision device is provided which comprises a two part assembly which traps the foreskin in between when it is put together. We prefer to the part which is first inserted along the shaft of the penis as a female part or member because upon assembly the other part i.e. the male member is inserted into it. The male member has an annular grooved ring which is placed underneath the foreskin and between it and the head of the penis. The female member also has a grooved ring which is positioned over the foreskin and in register with the ring under the foreskin so as to firmly grasp the same thereinbetween. This is possible because the outer ring has an adjustable inner circumference and can easily be compressed to exert pressure on the foreskin.

The structure of the device and its method of use will be more specifically explained by reference to the several figures of drawing attached hereto. FIG. 1 of the drawing is a perspective view of the female member of the assembly as it is first positioned on the shaft of the penis 14. FIG. 2 is also a perspective view and shows the male member now placed on the penis head 13 beneath the foreskin 12 while the female member in its expanded position is still in position on the shaft of the penis. FIG. 3 which is again a perspective view shows the two members in register with the end of the male member inserted in the circular orifice of the female member. Finally FIG. 4 discloses an exploded view of the construction of the male member tube and ring and the female member adjustable inside diameter ring.

Referring now to the FIGS. 1 to 4 of the drawings it can be seen in FIG. 1 that the female member comprises an expandable ring element having a distal rim 1 and proximate rim 5 with an annular groove 2 running completely around the circumference and outer surface of the ring. This ring has expansion spaces 3 and 3' therein which alternate with grasping fingers 4 so that pressure exerted on the outer surface of the ring causes the tips of the fingers 4 to move apart from one another and thus increase the internal diameter of the ring while a removal of such pressure causes the fingertips to come closer together and thus reduce the inside diameter of the ring.

In FIG. 1 also there is illustrated a compression clamp 16 a hinge 17 and a securing means made up of a latch 18 and a latch arm receptacle 19 and a pressure surface ring 20 of the said yoke. This surrounds entirely the female member such that the pressure surface area ring 20 fits snugly in the annular groove 2 of the female member and is latched into compressive location by means of the latch arm 18 snapped into the latch receptacle notch 19. When the compressive force is applied to the annular groove 2 it causes the grasping fingers to move apart and the ring has its interior diameter expanded. These expanded ring fingers 4 will eventually be placed over the foreskin 12 in register with the interior ring annular groove 8 which is beneath the foreskin with the distal rim 6 and proximal ring 7 of the inner ring insuring that the two rings stay in register.

the inner ring (6,7,8) is carried on the beveled edge 11 of a support tube 9 having an expansion joint 10 which is pushed over the head of the penis 13 by means of a push handle 15. This tube support carries the ring (6,7,8) underneath the foreskin 12 as illustrated in FIG. 2 of the drawing.

When this positioning of the male member tube 10 has been achieved the female assembly is moved up the shaft of the penis toward the head of the same until it comes into approximate register with the ring of the male member. At this point the female outer ring has pressure applied to its fingers 4 and expansion spaces 3 which alternate in the construction of the ring. This pressure is generated by the compressive clamp 16. Once these arms release their pressure by a release of the locking mechanism 18 and 19 the compressive force of these arms and compression ring 20 is lost. This loss of the compressive force causes the two rings to be drawn together as shown in FIG. 8 with the foreskin trapped in between. At this point the skin can be surgically excised and the rings hold the tissue together without suture. The rings stay on the shaft of the penis for several days to several weeks to enable the tissue of the foreskin to blend into and heal over into the remainder of skin on the penis.

The FIGS. 5 and 6 of the drawing show in greater detail the manner in which the compression of the pressure surface ring 20 on the outer skin holding ring rims 1 and 5 causes expansion of that ring while release of the compression causes the reverse effect to occur and the ring shrinks to hold the foreskin 12 firmly between the outer and inner skin holding rings. This is a very important aspect of this invention because it is this tissue which controls the bleeding of the cut foreskin tissue and the pressure on this tissue permits gradual healing of the wound without excessive bleeding and without recourse to suturing or other closure means. The way in which this works is that the fingers 4 spread apart in response to pressure from the pressure ring 20 and the expansion spaces 3 shrink. When this compression is released the fingers come together and the interior diameter of the ring reduces.

In FIGS. 7, 8 and 9 of the drawing their is shown an alternative embodiment of the invention wherein the outer skin holding female ring and the outer compressive clamp 16 are replaced by a wire spring 21 in the shape of a ring with two compressible handles 22a and 22b to permit it to be opened by two finger action of one hand. When 22a and 22b are pressed together the ring 21 expands and when the pressure is relaxed on 22a and 22b the ring contracts. Since the inner ring 23 is positioned on a male member 24 having a terminal recess 25 underneath the foreskin 12 the outer ring spring 21 and inner ring 23 are brought into register and outer ring 21 caused to compress. This traps the foreskin between the two. The excess foreskin is cut off and the male member 24 removed from beneath ring 23 forcing the cut end of the foreskin to be prevented from bleeding. After the ends have healed the rings 21 and 23 are removed in a few days time normally.

The concept of the present invention can ony be determined by the scope of the accompanying claims and all of the prior disclosure and illustrations in the drawings is simply to give concrete examples of that concept. For Example FIG. 10 of the drawing shows in an exploded view the relationship of the inner ring 23 which is superimposed on the male member 24 and the wire spring 21 which is outside the foreskin but traps it and holds it firmly once it comes into register with the grooved ring 23 and of course this grip persists after the male member 24 is slipped off. The spring 21 and the ring 23 fall off by themselves in a day or two after the tissue has healed.

I claim as my invention:

1. A circumcision device which comprises in combination a male and a female member, the male member comprised of tubular support means having imposed on the end thereof an annular grooved ring, said support means containing a means for slight flexure of the terminus on which the annular ring is mounted, the female member comprising a flexible plastic ring element capable of expansion or contraction of its internal diameter, said ring element having on its exterior face a distal rim and a proximal rim which define between them an annular groove, said ring element having a main body portion between the two rims which comprise alternating tissue grasping fingers and expansion spaces, a compression means which when applied to said distal rim and said proximal rim wedge the rims apart in an axial direction forcing the grasping fingers to expand radially outwardly and enlarge the bore of the ring element and when said compression means is removed to diminish the said bore by radially contracting the fingers of the ring element and exert compressive pressure on the tubular male member and its annular grooved ring.

2. A circumcision device according to claim 1 wherein the annular ring of the male member is frictionally attached to the support means at one end thereof.

3. A circumcision device according to claim 1 wherein the compression means are the jaws of a compression clamp.

4. A circumcision device according to claim 1 wherein the support means for the annular ring of the male member is a tubular support having a bevelled edge on one end thereof.

* * * * *